April 16, 1929. R. D. FOULKE Re. 17,271

FINGER SPLINT

Original Filed April 22, 1925

Roy D. Foulke, INVENTOR

BY

A. G. Burns ATTORNEY

Reissued Apr. 16, 1929. Re. 17,271

UNITED STATES PATENT OFFICE.

ROY D. FOULKE, OF WARSAW, INDIANA, ASSIGNOR TO WINIFRED DE PUY LEITER, OF WARSAW, INDIANA.

FINGER SPLINT.

Original No. 1,617,942, dated February 15, 1927, Serial No. 25,034, filed April 22, 1925. Application for reissue filed November 25, 1927. Serial No. 235,715.

This invention relates to improvements in surgical splints for injured digits, and the object thereof is to provide a structure that when applied to an injured finger will prevent bending of the finger at any of its joints including the knuckle joint, and which will shelter the extended end of the finger so that bumping of the end of the finger is obviated. Another object is to so form the splint that it will prevent lateral bending of the finger as well as the normal bending of the finger at its joints, and so that it is equally adaptable to anyone of the fingers of the hand. And a further object is to so form the splint as to permit longitudinal traction of the finger therein while confining the finger from bending, and so that treatment for the extension of the finger may be readily applied when so desired.

These objects are accomplished by the construction illustrated in the accompanying drawings, in which:—

The characters appearing in the description refer to parts shown in the drawings and designated thereon by corresponding characters.

Figure 1:
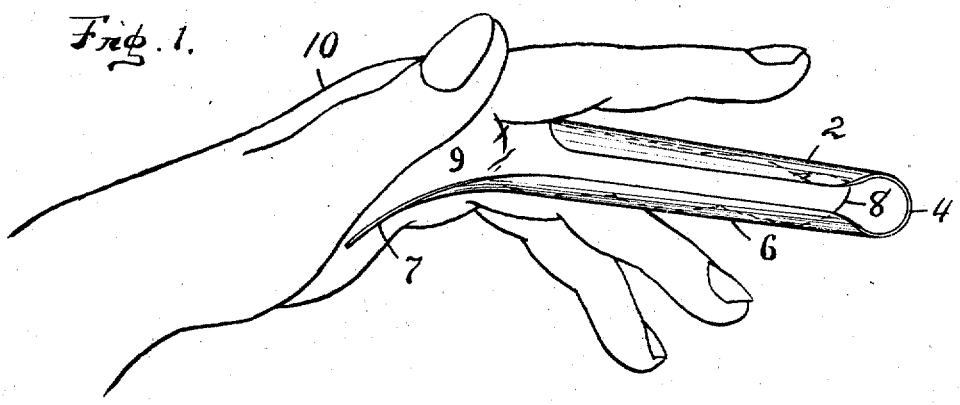
Fig. 1 is a perspective view of a hand with a splint applied thereto, in which the invention is embodied.
Figure 2:
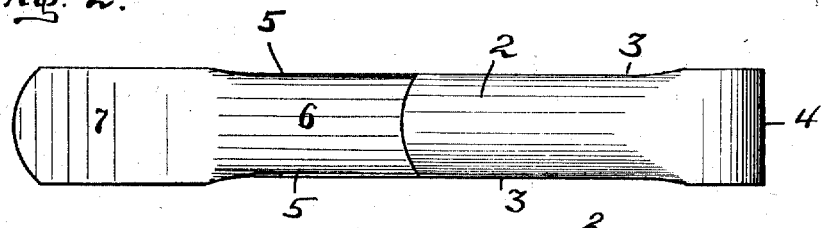
Fig. 2 is a plan view of the invention.
Figure 3:
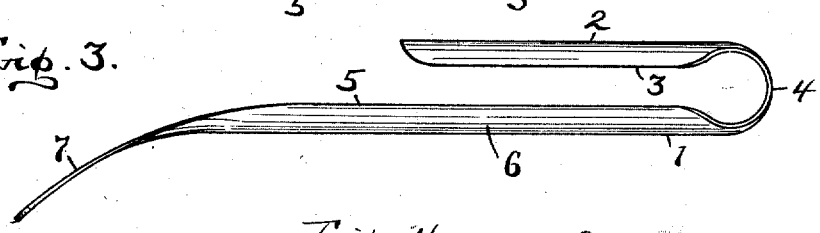
Fig. 3 is a side view projected from Fig. 2.
Figure 4:
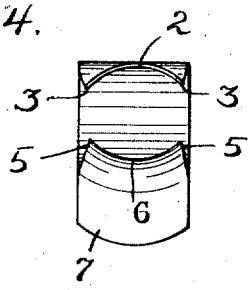
Fig. 4 is a rear end view of the same.

The invention comprises a splint formed of an elongated plate 1, preferably of metal, such as aluminum or such other material of such stiffness as will afford sufficient strength as to sustain the finger in its confined position in the splint, but which may be readily bent into the desired shape by applying greater force than that to which it will be subjected after the splint is applied. The plate is shaped with a top portion 2 that is transversely arched, its under face being concave, and its sides 3 inclined downwardly. Contiguous with the forward end of the cover is a loop 4 that forms a finger tip shelter, the plate being transversely straight at the front end of the loop. That portion of the plate contiguous with the lower part of the loop extends rearwardly therefrom and is transversely curved, its upper surface being concave and its sides 5 upwardly inclined so as to form a finger cradle 6. That portion of the plate at the rear end of the cradle is shaped with downward curvature and is transversely straight, and forms a palm rest 7, the upper surface of which is convex.

In utilizing the invention the splint is applied to the injured digit by placing the finger in the cradle with the cover extending over the tops of the finger joints, with the loop 4 extending beyond the finger tip 8 and with the rest 7 extending beneath the knuckle joint and in the palm 9 of the hand 10. The customary bandage (not shown) is applied to the injured finger and the splint in accordance with the practice of surgeons. When thus applied, the splint serves as a comfortable rest for the finger as it is supported by the hand to which the rest 7 is bandaged, and the cover 2 prevents the finger joints from moving upwardly. The sides 3 and 5 of the cover and cradle respectively partially cover the corresponding sides of the finger so that lateral bending of the finger is prevented. The hollow of the loop 4 at the end of the finger permits elongation of the finger, and the loop affords a shelter that prevents contact of an obstruction with the finger tip.

What I claim is:—

1. A finger splint formed of an elongated plate shaped with a cover portion that is longitudinally straight and transversely arched, its under face being concave and its sides inclined downwardly, a finger-tip sheltering loop contiguous with the forward end of said cover portion, a cradle portion contiguous with the lower end of the loop and extending rearwardly therefrom, its upper face being concave and its sides upwardly inclined, and that portion of the plate at the rear end of said cradle portion being shaped with downward longitudinal curvature so as to fit against the palm.

2. A finger splint formed of an elongated plate shaped with a cradle portion with upturned edges and a backwardly turned portion extending over said cradle portion having downwardly inclined sides and forming a cover for the top of a finger, and that portion of the plate contiguous with the rear end of said cradle portion being shaped with downward longitudinal curvature so as to fit against the palm of the hand when one of the fingers is inserted between said cradle and cover portions.

In testimony whereof I affix my signature.

ROY D. FOULKE.